(12) United States Patent
Dayton

(10) Patent No.: US 10,342,828 B1
(45) Date of Patent: Jul. 9, 2019

(54) FECAL OXYGENATION

(71) Applicant: Roderick M. Dayton, Strongsville, OH (US)

(72) Inventor: Roderick M. Dayton, Strongsville, OH (US)

( * ) Notice: Subject to any disclaimer, the term of this patent is extended or adjusted under 35 U.S.C. 154(b) by 28 days.

(21) Appl. No.: 15/635,158

(22) Filed: Jun. 27, 2017

Related U.S. Application Data

(60) Provisional application No. 62/354,840, filed on Jun. 27, 2016.

(51) Int. Cl.
  *A61K 33/40* (2006.01)
  *A61K 9/28* (2006.01)
  *A61K 9/00* (2006.01)
  *A61K 9/20* (2006.01)

(52) U.S. Cl.
  CPC ............ *A61K 33/40* (2013.01); *A61K 9/0053* (2013.01); *A61K 9/2072* (2013.01); *A61K 9/28* (2013.01)

(58) Field of Classification Search
  CPC ......... A61J 33/40; A61K 9/28; A61K 9/0053; A61K 33/40
  See application file for complete search history.

(56) References Cited

U.S. PATENT DOCUMENTS 6,110,443 A * 8/2000 Schneider ............ A61K 49/223
    424/450
2016/0030596 A1* 2/2016 Kheir .................. A61K 9/5031
    424/489

OTHER PUBLICATIONS

Wainwright et al., Antimicrobial photodynamic therapy in the colon: delivering a light punch to the guts? Photochem Photobiol. Jul. 2011 ; 87(4): 754-756 (Year: 2011).*
Jain et al., Perspective of Biodegradable Natural Polysaccharides for Site-Specific Drug Delivery to the Colon, J Pharm Pharmaceut Sci (www. cspsCanada.org) 10 (1): 86-128, (Year: 2007).*

* cited by examiner

*Primary Examiner* — Michael G. Hartley
*Assistant Examiner* — Nabila G Ebrahim
(74) *Attorney, Agent, or Firm* — Kraguljac Law Group, LLC

(57) ABSTRACT

Provided are a device and method for oxygenating fecal matter in a patient. The device includes an interior material defining a plurality of oxygen packets including oxygen to be introduced into the patient's digestive tract. An outer coating applied to an exterior of the interior material protects the interior material from an environment of the patient's digestive tract when the device is consumed, and is dissolved by a substance within the patient's digestive tract to expose the interior material to the patient's digestive tract after a delay.

6 Claims, 1 Drawing Sheet

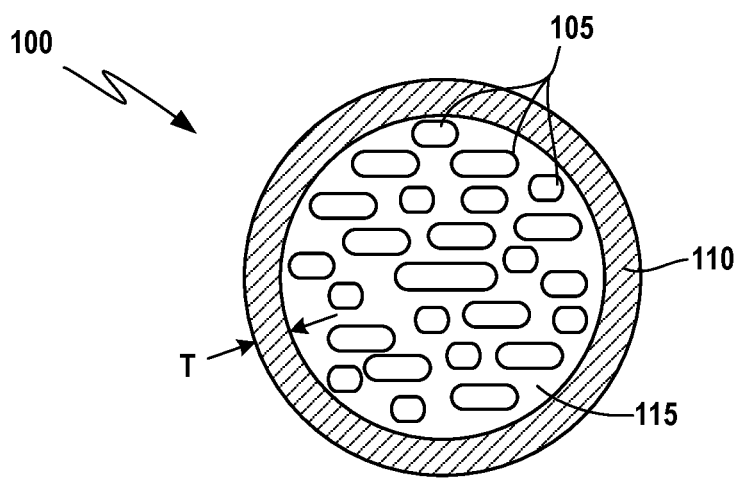

US 10,342,828 B1

FECAL OXYGENATION

BACKGROUND OF THE INVENTION

Field of the Invention

This application relates generally to a method and composition for treating an infection and, more specifically, a method and composition for in vivo exposure of bacteria to oxygen.

Description of Related Art

*Clostridium difficile*, referred to herein as "Cdiff," is a significant pathogen with a very high mortality rate for immunocompromised patients. In the presence of oxygen, Cdiff becomes a self-protecting spore that can live for many months in a suspended state, awaiting reentry into a moist, no oxygen environment, like the lower intestines of a human. One conventional method for dealing with a Cdiff infection is transplanting another person's processed feces into the colon of the infected person. The intention is to "dilute" the Cdiff with the more beneficial flora of the healthy person's feces. This procedure is commonly referred to as a fecal transplant. Although fecal transplants can be effective, the procedure is invasive and can be a lengthy process to effectively treat the Cdiff infection.

BRIEF SUMMARY OF THE INVENTION

According to one aspect, the subject application involves a device and method for oxygenating fecal matter in a patient. The device includes an interior material defining a plurality of oxygen packets including oxygen to be introduced into the patient's digestive tract. An outer coating applied to an exterior of the interior material protects the interior material from an environment of the patient's digestive tract when the device is consumed, and is dissolved by a substance within the patient's digestive tract to expose the interior material to the patient's digestive tract after a delay.

According to another aspect, the subject application involves administering a device for oxygenating fecal matter in a patient to the patient orally, rectally, or via another route. Encapsulated oxygen packets are protected from the environment within the patient's digestive tract, approximately until a time when the device enters a region of the digestive tract where fecal matter is located. While exposed to the fecal matter within the digestive tract, an interior material that was previously shielded is dissolved, releasing the oxygen content within the oxygen packet into the fecal matter.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein:

FIG. 1 shows a schematic sectional view of a pill including a plurality of oxygen packets to be released in a colon of a patient to oxygenate fecal matter;

DETAILED DESCRIPTION OF THE INVENTION

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

There is a need in the art for a method and composition for treating a *Clostridium difficile* ("Cdiff") infection, and possibly other oxygen-sensitive infections, with a time-delayed release of oxygen. Using Cdiff as an example of a treatable infection, Cdif does not thrive in the presence of air or other oxygen-rich environment. Accordingly, the present disclosure involves introducing air or other source of oxygen to a region of a human body where the Cdiff infection resides, to reduce the volume of thriving Cdiff present. The oxygen can be introduced to the affected region via an oral, rectal, or any other suitable route. The oxygen can be introduced encapsulated in a shell that can deteriorate in the presence of bodily fluids or other substances present in and around the region where the Cdiff bacteria are present and along the route of administration to the region where the Cdiff bacteria are present.

According to a method, oxygen can be introduced to the infected Cdiff region, such as in the large intestine and colon, optionally using a catheter type arrangement where oxygen is pumped into the large intestine, color or other region located in the lower portion of the patient. According to another embodiment, fecal transplant material that is to be transplanted into a patient can optionally be oxygenated (e.g., oxygen is introduced to the fecal material to elevate the amount of oxygen present to levels above the oxygen level naturally present in the fecal transplant material prior to the introduction of the oxygen). Introducing oxygen into the material itself is believed to provide some benefit, but the volume and longevity of the oxygen in this configuration may be limited to an extent that renders the present embodiment of limited usefulness.

According to alternate embodiments, the present disclosure is directed towards a method and composition to provide a prolonged release of oxygen into the Cdiff-affected zone (e.g., the large intestine, colon and other regions that would otherwise be affected by a fecal transplant). One embodiment of the present method involves introducing and embedding encapsulated oxygen into the fecal transplant material that is to be transplanted into a patient. Encapsulated oxygen can include oxygen-rich substances such as air, purified oxygen, etc. encapsulated within a shell that dissolves, degrades, or otherwise changes to release the encapsulated oxygen. Based at least in part on the properties of the shell, the oxygen can be released from the shell over a predetermined period of time, and/or begin to release the encapsulated oxygen after a predetermine threshold period of time has expired from a time when the encapsulated oxygen is introduced to the fecal transplant material, the infected patient, or both. For example, the thicknesses of shell material encapsulating the "oxygen packets", that, due to their thickness and corresponding varying times required to dissolve, cause a time delay from when the shell is introduced to the fecal transplant material or patient before the oxygen is released from the shell. According to alternate embodiments, the specific chemical composition of the shell material itself can be configured to establish the desired time-delayed aspects of the encapsulated oxygen. Yet other embodiments utilize a combination of the shell structure (e.g., thickness) and the shell composition (e.g., chemical composition) to control the delay between when encapsulated oxygen is introduced to the fecal material and/or patient and a time when the oxygen release begins, and/or to control the duration of the oxygen release.

With reference to the drawings, FIG. 1 shows an embodiment of a pill 100 including encapsulated oxygen packets 105. An outer coating 110 of the pill 100 encapsulates an interior material 115 defining the oxygen packets 105. The outer coating 110 can be formed from a first material that dissolves at a known rate within the digestive tract of the patient when consumed orally. The first material forming the outer coating 110 can be approved by a government regulatory body (e.g., U.S. Food and Drug Administration) for human consumption. The outer coating 110 can also be formed with a thickness T to enable the outer coating 110 to remain substantially intact as the pill 100 travels along the patient's digestive tract, through the patient's stomach. For example, the outer coating 110 can optionally encapsulate the interior material 115 (e.g., shield the interior material 115 from exposure to bodily fluids of the patient) for at least four (4) hours, or at least six (6) hours, or at least eight (8) hours from a time when the device is ingested. At about the time when the pill 100 reaches or approaches the top of the patient's colon, the outer coating 110 can be at least partially, and optionally mostly or fully dissolved, degraded, or otherwise compromised to at least begin exposing a portion of the interior material 115 to the environment within the colon. For example, the outer coating 110 can be formed from materials such as a guargum or chewing gum type substance that is able to withstand gastric acids and make its way until shortly before, or shortly after entering the colon along the digestive tract.

The interior material 115 defines therein a plurality of oxygen packets 105 in which air (having an oxygen concentration of about 21% by volume), purified oxygen (e.g., having an oxygen concentration of greater than 21% by volume, or greater than 40% by volume, or greater than 60% by volume, or greater than 80% by volume, or greater than 90% by volume). The interior material 115 can be formed from a second material, different than the first material, and dissolves at a known rate within the digestive tract of the patient when consumed orally. The second material forming the interior material 115 can be approved by a government regulatory body for human consumption. The oxygen packets 105 can optionally be substantially uniform in dimensions and/or volume, or can vary in dimensions and/or volume. For embodiments where the dimensions and/or volumes vary, the oxygen packets 105 can be distributed according to a patter. For example, oxygen packets 105 with relatively large volumes of oxygen can optionally be arranged adjacent to a center of the interior material 115, and oxygen packets 105 with relatively small volumes of oxygen can optionally be arranged adjacent to an outer periphery of the interior material 115. For such an embodiment, a greater volume of oxygen is released from the oxygen packets 105 as the interior material 115 dissolves, degrades or is otherwise consumed from the outside toward a central region in within the colon. Of course the oxygen packets 105 can be arranged in any desired pattern without departing from the scope of the present disclosure.

As noted above, the outer coating 110 can be configured in thickness, chemical composition, etc., to last and protect the interior material 115 and encapsulated oxygen packets 1005 through the digestive tract until the pill 100 makes its way to the vicinity of the top of the colon. Similarly, the interior material 115 can be configured in dimensions, chemical composition, density, etc. to continuously dissolve, degrade or otherwise release the oxygen packets 105 for at least a portion of the time the pill 100 travels through the colon. The interior material 115 separating the oxygen packets 105 can also be defined with varying dimensions (e.g., thickness) to regulate the length of time over which the oxygen packets 105 are released. Thinner interior material dimensions between oxygen packets 105 will cause the oxygen packets 105 to be released in close succession, allowing the oxygen to escape sooner in the digestive tract, while thicker interior material dimensions will space out the oxygen releases and take longer for all oxygen packets 105 to be released. In this way a continual dose can be provided over time as the pill 100 makes its way through the body system, releasing oxygen as it goes.

According to alternate embodiments, the interior material 115 can be configured in composition and dimensions to dissolve, degrade or otherwise release most of the oxygen packets 105 in response to entering the colon and being exposed to the patient's fecal matter. For example, the composition of the interior material 115 can include a time-release substance that slows a rate at which the interior material 115 degrades within the digestive tract to a slower rate. The slower rate of degradation can be slower than the natural rate of degradation of the interior material 115 without the time-release component. Such a pill 100 can release the encapsulated oxygen packets 105 to oxygenate the patient's fecal matter early in the colon, potentially increasing the time the patient's fecal matter is exposed to pure, or substantially-pure oxygen. The release of oxygen can then continue for as long as the interior material 115 defines oxygen packets 105 that have yet to be compromised.

Although described above as an orally ingestible pill 100, the pill 100 can optionally be configured as a rectally inserted suppository that is much larger and contains more oxygen packets 105 than a pill 100 taken by mouth. Rectal insertion of such a pill 100 can be done in a hospital setting, or at another healthcare facility where medical treatment is administered. Further, because such a pill 100 does not necessary have to withstand exposure to stomach acids, etc. before reaching the colon, the outer coating 110 for the suppository can optionally be configured (e.g., chemical composition and/or dimensions) expose the interior material 115 sooner upon introduction into the patient than a pill 100 consumed orally.

Another embodiment involves surgical attachment of the suppository embodiment of the pill 100 to the inner wall of the colon with a dissolvable suture that holds this pill 100 in place long enough for all, or at least a portion of the oxygen packets 105 to be released before being passed.

According to alternate embodiments, the pill 100 can also optionally encapsulate a high organic load, fiber and/or other nutritional, medicinal and/or therapeutic component (referred to as an "additive") to help promote a healthy population of bacteria within the colon. The additive chosen can optionally flourish under the increased oxygen content of the patient's fecal matter, providing additional benefit to fighting the Cdiff infection by further diluting the Cdiff concentration, and promoting desired bowel function.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A device for introducing oxygen to a portion of a patient's digestive tract, the device comprising:
    an interior material defining a plurality of oxygen packets including oxygen to be introduced into the patient's digestive tract, wherein the oxygen concentration within the oxygen packets is at least 40% by volume; and
    an outer coating applied to an exterior of the interior material, wherein the outer coating protects the interior material from an environment of the patient's digestive tract, and is dissolved by a substance within the patient's digestive tract to expose the interior material to the patient's digestive tract after a delay, wherein the device is in the form of an orally ingestible pill or configured as a suppository.

2. The device of claim 1, wherein the interior material comprises a time-release material that retards a rate of degradation of the interior material in the patient's digestive tract from a natural rate at which the interior material degrades without the time-release material.

3. The device of claim 1, wherein the oxygen packets defined by the interior material store a plurality of different volumes.

4. The device of claim 1, wherein the oxygen concentration of the oxygen within the oxygen packets is at least 60% by volume.

5. The device of claim 1, wherein the outer coating encapsulates the interior material for at least four (4) hours from a time when the device is ingested.

6. The device of claim 1 further comprising an additive comprising at least one of: concentrated fiber, a nutrient, a medicinal substance, and a therapeutic component.

* * * * *